United States Patent [19]

Furutaka et al.

[11] Patent Number: 4,739,123

[45] Date of Patent: Apr. 19, 1988

[54] FLUORINE-CONTAINING COMPOUNDS, AND THEIR PREPARATION AND USE

[75] Inventors: Yasuhisa Furutaka, Takatsuki; Masayuki Yamana; Tsunetoshi Honda, both of Settsu, all of Japan

[73] Assignee: Daiken Industries, Ltd., Osaka, Japan

[21] Appl. No.: 921,207

[22] Filed: Oct. 21, 1986

[30] Foreign Application Priority Data

Oct. 21, 1985 [JP] Japan .............................. 60-235967
Oct. 21, 1985 [JP] Japan .............................. 60-235968

[51] Int. Cl.$^4$ ............................................. C07C 17/00
[52] U.S. Cl. ..................................... 570/142; 570/153
[58] Field of Search ................................. 570/153, 142

[56] References Cited

FOREIGN PATENT DOCUMENTS 194825 11/1983 Japan .................................. 570/136

OTHER PUBLICATIONS

Nokanishi et al., JACS 77, 3099 (1955).

*Primary Examiner*—Donald B. Moyer
*Assistant Examiner*—Joseph A. Boska
*Attorney, Agent, or Firm*—Birch, Stewart, Kolasch & Birch

[57] ABSTRACT

Process for preparing 2-trifluoro-methyl-3,3,3-trifluoropropene.

2 Claims, No Drawings

FLUORINE-CONTAINING COMPOUNDS, AND THEIR PREPARATION AND USE

FIELD OF THE INVENTION

The present invention relates to fluorine-containing compounds, and their preparation and use. More particularly, it relates to novel chloromethyl 2-trifluoromethyl-3,3,3-trifluoropropanoates, and their preparation and use.

BACKGROUND OF THE INVENTION

2-Trifluoromethyl-3,3,3-trifluoropropene is an interesting compound as a monomer for production of various polymers. For instance, it is copolymerized with vinylidene fluoride to produce a vinylidene fluoride/2-trifluoromethyl-3,3,3-trifluoropropene alternating copolymer having good heat resistance (Japanese Patent Publication No. 28210/1984). Further, for instance, its incorporation as a monomeric unit into an ethylene/tetrafluoroethylene copolymer produces marked improvement in physical properties (Japanese Patent Publication No. 25806/1984).

For production of said 2-trifluoromethyl-3,3,3-trifluoropropene, there has been known a process wherein hexafluoroacetone and acetic anhydride or ketene are subjected to pyrolysis (Japanese Patent Publication No. 35168/1983). However, this process is industrially disadvantageous, because hexafluoroacetone as the starting material is quite expensive and drastic conditions are required for the pyrolysis. There has also been known a process wherein octafluoroisobutyl lower alkyl ether is dehydrofluorinated, the resulting heptafluoroisobutenyl lower alkyl ether is reduced to hexafluoroisobutyl lower alkyl ether, and the latter is sulfated to produce hexafluoroisobutyl lower alkyl sulfate, which is then treated with a base to give 2-trifluoromethyl-3,3,3-trifluoropropene (Japanese Patent Publication No. 6133/1982). Apparently, this process requires many steps and necessitates the use of various reagents and equipments.

SUMMARY OF THE INVENTION

As a result of the extensive study, it has been found that 2-trifluoromethyl-3,3,3-trifluoropropene can be produced easily and economically from monochloromethyl 2-trifluoromethyl-3,3,3-trifluoropropanoate, which is new and can be readily prepared, for instance, from methyl 2-trifluoromethyl-3,3,3-trifluoropropanoate or 1-chloromethoxy-1,1-difluoro-2-trifluoromethyl-3,3,3-trifluoropropane.

A main object of the present invention is to provide an industrially advantageous process for producing 2-trifluoromethyl-3,3,3-trifluoropropene in a high yield with a low cost. Another object of this invention is to provide novel fluorine-containing compounds, i.e. chloromethyl 2-trifluoromethyl-3,3,3-trifluoropropanoates, which are useful as intermediates in the production of 2-trifluoromethyl-3,3,3-trifluoropropene. A further object of the invention is to provide processes for preparing said novel fluorine-containing compounds.

The novel fluorine-containing compounds of the invention are representable by the formula:

    (I)

wherein $X^1$ and $X^2$ are, the same or different, each a hydrogen atom or a chlorine atom and include specifically monochloromethyl 2-trifluoromethyl-3,3,3-trifluoropropanoate, dichloromethyl 2-trifluoromethyl-3,3,3-trifluoropropanoate and trichloromethyl 2-trifluoromethyl-3,3,3-trifluoropropanoate.

The fluorine-containing compounds (I) may be prepared by contacting methyl 2-trifluoromethyl-3,3,3-trifruoropropanoate with chlorine under irradiation with light. Monochloromethyl 2-trifluoromethyl-3,3,3-trifluoropropanoate as one of the fluorine-containing compounds (I) may be also prepared by hydrolyzing 1-chloromethoxy-1,1-difluoro-2-trifluoromethyl-3,3,3-trifluoropropane in the presence of an acid catalyst.

Reaction of monochloromethyl 2-trifluoromethyl-3,3,3-trifluoropropanoate with an amine gives 2-trifluoromethyl-3,3,3-trifluoropropene.

DETAILED DESCRIPTION OF THE INVENTION

The fluorine-containing compounds (I) are produced by contacting methyl 2-trifluoromethyl-3,3,3-trifruoropropanoate with chlorine under irradiation with light. The above chlorination may be carried out in a liquid or gaseous phase. As the light source in the chlorination, there may be used a mercury vapor lamp, a xenon lamp or the like. The temperature for chlorination is usually from about 0° to 400° C., preferably from about 0 to 90° C. The pressure may be kept at a normal or slightly elevated pressure.

The starting methyl 2-trifluoromethyl-3,3,3-trifluoropropanoate may be produced, for instance, by hydrolyzing 1-methoxy-1,1-difluoro-2-trifluoromethyl-3,3,3-trifluoropropane in the presence of an acid catalyst (e.g. sulfuric acid, fluorosulfuric acid, trifluoromethanesulfonic acid).

Among the fluorine-containing compounds (I), monochloromethyl 2-trifluoromethyl-3,3,3-trifluoropropanate may be also produced by hydrolyzing 1-chloromethoxy-1,1-difluoro-2-trifluoromethyl-3,3,3-trifluoropropane in the presence of an acid catalyst. The hydrolysis is carried out in the presence of water or any oxide (e.g. silicon dioxide) by the use of an acid catalyst (e.g. sulfuric acid, fluorosulfuric acid, trifluoromethanesulfonic acid), usually at a temperature of about 20° to 200° C. for a period of about 0.5 to 50 hours. The amount of water to be used may be from 1 to 10 mol per 1 mol of 1-chloromethoxy-1,1-difluoro-2-trifluoromethyl-3,3,3-trifluoropropane. The amount of the acid catalyst is used in an amount of 0.0001 to 2 mol per 1 mol of 1-chloromethoxy-1,1-difluoro-2-trifluoromethyl-3,3,3-trifluoropropane.

The starting 1-chloromethoxy-1,1-difluoro-2-trifluoromethyl-3,3,3-trifluoropropane may be produced, for example, by chlorinating 1-methoxy-1,1-difluoro-2-trifluoromethyl-3,3,3-trifluoropropane under irradiation with light.

Among the thus produced fluorine-containing compounds (I), monochloromethyl 2-trifluoromethyl-3,3,3-trifluoropropanoate is reacted with an amine to give 2-trifluoromethyl-3,3,3-trifluoropropene in a high yield.

As the amine, there may be used triethylamine, tripropylamine, tributylamine, pyridine, picoline, tetramethylethylenediamine, diazabicycloundecene, diethylamine, dibutylamine, propylamine, butylamine, ethylenediamine or the like. The amount of the amine is usually from 1.0 to 20.0 mol per 1 mol of the fluorine-containing compound. The reaction proceeds at a temperature of about 30° to 200° C., preferably of about 50° to 150° C., for a period of about 0.5 to 10 hours, preferably of about 1 to 5 hours.

The present invention will be explained further in detail by the following examples.

EXAMPLE 1

In a four necked 200 ml Pyrex flask equipped with a condenser and a tube for injecting chlorine, methyl 2-trifluoromethyl-3,3,3-trifluoropropanoate (105 g, 500 mmol) was charged. Chlorine was injected into the flask from the tube at a rate of 44.8 ml/min (2.0 mmol/min) under irradiation with a 75 W high-pressure mercury vapor lamp. The reaction was continued at 72° C. for 6.5 hours. Then, the reaction mixture was fractionally distilled to give monochloromethyl 2-trifluoromethyl-3,3,3-trifluoropropanoate (b.p., 120° C.) (37.5 g), dichloromethyl 2-trifluoromethyl-3,3,3-trifluoropropanoate (b.p., 125° C.) (64.0 g) and trichloromethyl 2-trifluoromethyl-3,3,3-trifluoropropanoate (b.p., 147° C.) (1.5 g). Unreacted methyl 2-trifluoromethyl-3,3,3-trifluoropropanoate was not recovered.

EXAMPLE 2

In the same manner as Example 1, methyl 2-trifluoromethyl-3,3,3-trifluoropropanoate (105 g, 500 mmol) was charged. Chlorine was injected into the flask at a rate of 22.4 ml/min (1.0 mmol/min) under irradiation with a 75 W high-pressure mercury vapor lamp. The reaction was continued at 70° C. for 7 hours. Then, the reaction mixture was fractionally distilled to give monochloromethyl 2-trifluoromethyl-3,3,3-trifluoropropanoate (71.4 g) and dichloromethyl 2-trifluoromethyl-3,3,3-trifluoropropanoate (13.2 g). Unreacted methyl 2-trifluoromethyl-3,3,3-trifluoropropanoate (19.7 g) was simultaneously recovered.

EXAMPLE 3

In a four necked 1 liter flask equipped with a thermometer, a condenser and a stirrer, 1-chloromethoxy-1,1-difluoro-2-trifluoromethyl-3,3,3-trifluoropropane (276.6 g, 1.04 mol) and silicon dioxide (50.8 g, 0.85 mol) were charged, and concentrated sulfuric acid (60 g, 0.61 mol) was dropwise added thereto while stirring. The reaction was continued at 110° C. for 21 hours. Then, the reaction mixture was distilled to give monochloromethyl 2-trifluoromethyl-3,3,3-trifluoropropanoate (192.9 g).

EXAMPLE 4

In a four necked 1 liter flask equipped with a thermometer, a condenser and a stirrer, 1-chloromethoxy-1,1-difluoro-2-trifluoromethyl-3,3,3-trifluoropropane (276.6 g, 1.04 mol) and water (18.7 g, 1.04 mol) were charged, and concentrated sulfuric acid (74.8 g, 0.76 mol) was dropwise added thereto while stirring. The reaction was continued at 110° C. for 20 hours. Then, the reaction mixture was distilled to give monochloromethyl 2-trifluoromethyl-3,3,3-trifluoropropanoate (187.8 g).

EXAMPLE 5

In a four necked 1 liter flask equipped with a thermometer, a condenser and a stirrer, 1-chloromethoxy-1,1-difluoro-2-trifluoromethyl-3,3,3-trifluoropropane (276.6 g, 1.04 mol), silicon dioxide and fluorosulfuric acid (70.0 g, 0.70 mol) were charged. The reaction was continued at 110° C. for 21 hours. Then, the reaction mixture was distilled to give monochloromethyl 2-trifluoromethyl-3,3,3-trifluoropropanoate (190.3 g).

EXAMPLE 6

In a four necked 100 ml flask equipped with a condenser, a dropping funnel and a thermometer, pyridine (19.3 g, 244 mmol) was charged and warmed to 70° C. Monochloromethyl 2-trifluoromethyl-3,3,3-trifluoropropanoate (4.88 g, 20 mmol) was dropwise added thereto while stirring. The reaction was continued at the same temperature as above for 2 hours while stirring. The gas evolved from a top of the condenser was washed with an alkaline solution, dried with alumina and cooled. The resultant liquid was distillated to give 2-trifluoromethyl-3,3,3-trifluoropropene (b.p., 14° C.) (2.30 g). Yield, 70 %.

EXAMPLE 7

In a four necked 100 ml flask equipped with a condenser, a dropping funnel and a thermometer, triethylamine (20.0 g, 198 mmol) was charged and warmed to 60° C. Monochloromethyl 2-trifluoromethyl-3,3,3-trifluoropropanoate (4.88 g, 20 mmol) was dropwise added thereto while stirring. The reaction was continued at the same temperature as above for 2.5 hours while stirring. The gas evolved from a top of the condenser was washed with an alkaline solution, dried with alumina and cooled. The resultant liquid was distilled to give 2-trifluoromethyl-3,3,3-trifluoropropene (2.36 g). Yield, 72 %.

EXAMPLE 8

In a four necked 100 ml flask equipped with a condenser, a dropping funnel and a thermometer, tributylamine (20.0 g, 108 mmoles) was charged and warmed to 65° C. Monochloromethyl 2-trifluoromethyl-3,3,3-trifluoropropanoate (4.88 g, 20 mmol) was dropwise added thereto while stirring. The reaction was continued at the same temperature as above for 3 hours while stirring. The gas evolved from a top of the condenser was washed with an alkaline solution, dried with alumina and cooled. The resultant liquid was distilled to give 2-trifluoromethyl-3,3,3-trifluoropropene (2.49 g). Yield, 76 %.

What is claimed is:

1. A process for preparing 2-trifluoromethyl-3,3,3-trifluoropropene, which comprises reacting monochloromethyl 2-trifluoromethyl-3,3,3-trifluoropropanoate with an amine.

2. A process according to claim 1, wherein the reaction is effected at a temperature of 30° to 200° C.

* * * * *

UNITED STATES PATENT AND TRADEMARK OFFICE
CERTIFICATE OF CORRECTION

PATENT NO. : 4,739,123
DATED : April 19, 1988
INVENTOR(S) : Yasuhisa FURUTAKA, et al It is certified that error appears in the above-identified patent and that said Letters Patent is hereby corrected as shown below:

On the front page of the patent, Column 1, at item [73], please correct the name of the Assignee to --Daikin Industries, Ltd.--.

Signed and Sealed this

Fourth Day of October, 1988

*Attest:*

DONALD J. QUIGG

*Attesting Officer*  *Commissioner of Patents and Trademarks*